US010038865B2

(12) United States Patent
Kagawa et al.

(10) Patent No.: US 10,038,865 B2
(45) Date of Patent: Jul. 31, 2018

(54) COMMUNICATION SYSTEM

(71) Applicant: OLYMPUS CORPORATION, Tokyo (JP)

(72) Inventors: Ryohei Kagawa, Hachioji (JP); Hidetsugu Takahashi, Hachioji (JP); Manabu Ishizeki, Hino (JP); Hidetaro Kono, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/479,338

(22) Filed: Apr. 5, 2017

(65) Prior Publication Data
US 2017/0208275 A1    Jul. 20, 2017

Related U.S. Application Data

(63) Continuation of application No. PCT/JP2015/085511, filed on Dec. 18, 2015.

(30) Foreign Application Priority Data

Dec. 25, 2014  (JP) ................................. 2014-263188

(51) Int. Cl.
*H04N 5/38* (2006.01)
*H03K 19/00* (2006.01)
(Continued)

(52) U.S. Cl.
CPC ............... *H04N 5/374* (2013.01); *A61B 1/04* (2013.01); *G02B 23/2484* (2013.01); *H03K 19/17748* (2013.01); *H04N 5/38* (2013.01)

(58) Field of Classification Search
CPC . H04N 5/374; H04N 5/38; A61B 1/04; G02B 23/2484; H03K 19/17748
See application file for complete search history.

(56) References Cited

U.S. PATENT DOCUMENTS 5,812,796 A    9/1998  Broedner et al.
6,448,810 B1   9/2002  Nomura
(Continued)

FOREIGN PATENT DOCUMENTS

EP    1 071 998 A1    1/2001
JP    H05-075583 A    3/1993
(Continued)

OTHER PUBLICATIONS

International Search Report dated Feb. 9, 2016 issued in PCT/JP2015/085511.
(Continued)

*Primary Examiner* — Tim T Vo
*Assistant Examiner* — Harry Wang
(74) *Attorney, Agent, or Firm* — Scully, Scott, Murphy & Presser, P.C.

(57) ABSTRACT

A communication system includes: a first signal line; a second signal line; a first signal line selection portion and a second signal line selection portion for selecting either one of the first signal line and the second signal line so as to be effective as the serial data; and a signal control portion for outputting a signal direction switching signal for controlling a selecting operation. The first signal line selection portion includes a first OR circuit and a first three-state buffer circuit provided on the first signal line, and a first buffer provided on the second signal line, and the second signal line selection portion includes a second OR circuit and a second three-state buffer circuit provided on the second signal line, a second buffer provided on the first signal line, and an inverter circuit provided between a terminal of the signal control portion and the second OR circuit.

10 Claims, 5 Drawing Sheets

(51) Int. Cl.
*H04N 5/374* (2011.01)
*A61B 1/04* (2006.01)
*G02B 23/24* (2006.01)
*H03K 19/177* (2006.01)

(56) References Cited

U.S. PATENT DOCUMENTS

2003/0197528 A1   10/2003   Shibata et al.
2013/0170575 A1   7/2013   Imai et al.

FOREIGN PATENT DOCUMENTS

| JP | H06-224976 A | 8/1994 |
| JP | 2012-195639 A | 10/2012 |
| JP | 5356632 B1 | 12/2013 |

OTHER PUBLICATIONS

Extended Supplementary European Search Report dated May 15, 2018 in European Patent Application No. 15 87 2937.6.

FIG. 2

| T | I | I/O | O |
|---|---|-----|---|
| 1 | X | Z | I/O |
| 0 | 1 | 1 | 1 |
| 0 | 0 | 0 | 0 |

COMMUNICATION SYSTEM

CROSS REFERENCE TO RELATED APPLICATION

This application is a continuation application of PCT/JP2015/085511 filed on Dec. 18, 2015 and claims benefit of Japanese Application No. 2014-263188 filed in Japan on Dec. 25, 2014, the entire contents of which are incorporated herein by this reference.

BACKGROUND OF THE INVENTION

1. Field of the Invention

The present invention relates to a communication system in an endoscope system including an endoscope loaded with a CMOS sensor as an image pickup device.

2. Description of the Related Art

Conventionally, as a general-purpose serial connection system for connecting a plurality of elements by communication, a serial communication standard referred to as so-called I2C (inter-integrated circuit) is known.

The I2C is a synchronous type serial communication standard of performing communication by two bidirectional open collector signal lines (serial data SDA and serial clock SCL) pulled up by a resistor, and write to a specified device and read are performed using the SDA and SCL. The SDA and SCL are both bus signals and the plurality of elements are connected by the bus in the I2C.

Then, in the I2C, a master that requests read and write of data utilizing the bus signals of the SDA and SCL and a slave that receives and sends out the data according to requests of the master are provided, and the plurality of slaves can be connected to the bus further. In addition, the master selects a slave by specifying an individually determined address of the slave and then communicates with the slave.

On the other hand, conventionally, an endoscope including an image pickup device has been widely used in a medical field and an industrial field. In addition, a technique of configuring an endoscope system in which a signal processing device referred to as a processor is freely attachably and detachably connected to the endoscope and bears various kinds of signal processing relating to the endoscope is also known.

In addition, in recent years, an endoscope adopting a CMOS sensor as an image pickup device has been also proposed. The CMOS sensor of the kind includes an A/D conversion portion together with an image pickup portion inside a sensor chip of the CMOS sensor, and an output signal as the sensor is a digital signal.

Then, in the endoscope system including the endoscope adopting the CMOS sensor of the kind, a technique of performing communication control between the CMOS sensor and a processor which is a signal processing portion by the I2C described above is known (Japanese Patent No. 5356632).

Now, in a case of the endoscope system adopting the CMOS sensor at an endoscope distal end, which performs the communication control by the I2C described above, a configuration that the CMOS sensor is one of the slaves and the master is mounted on the processor is conceivable.

In the case of such an endoscope system, the CMOS sensor disposed at an endoscope distal end portion and the processor are connected by a cable having a length of several meters, however, it means that the CMOS sensor which is one of the slaves and the processor which is the master are connected by the cable of several meters.

SUMMARY OF THE INVENTION

A communication system of one aspect of the present invention is the communication system in which a slave device and a master device configured to transmit and receive data to/from the slave device by specifying an address are connected by a clock signal line configured to convey a clock transmitted from the master device and a serial data signal line configured to bidirectionally transmit data, and includes: a first signal line configuring a portion of the serial data signal line and configured to transmit predetermined data from the master device to the slave device; a second signal line configuring a portion of the serial data signal line and configured to transmit predetermined data from the slave device to the master device; a signal line selection portion configured to select either one of the first signal line and the second signal line so as to be effective as the serial data signal line; and a signal control portion including a terminal configured to output a signal direction switching signal for controlling the selecting operation in the signal line selection portion. The signal line selection portion is configured by a first signal line selection portion and a second signal line selection portion, the first signal line selection portion includes a first OR circuit and a first three-state buffer circuit provided on the first signal line, and a first buffer provided on the second signal line, and the second signal line selection portion includes a second OR circuit and a second three-state buffer circuit provided on the second signal line, a second buffer provided on the first signal line, and an inverter circuit provided between the terminal of the signal control portion and the second OR circuit.

BRIEF DESCRIPTION OF THE DRAWINGS

FIG. 2 is a diagram illustrating a truth table of a logic circuit of a bus signal direction switching mechanism of serial data SDA in the endoscope system of the first embodiment;

DETAILED DESCRIPTION OF THE PREFERRED EMBODIMENT(S)

Hereinafter, an embodiment of the present invention will be described with reference to the drawings.

Figure 1:
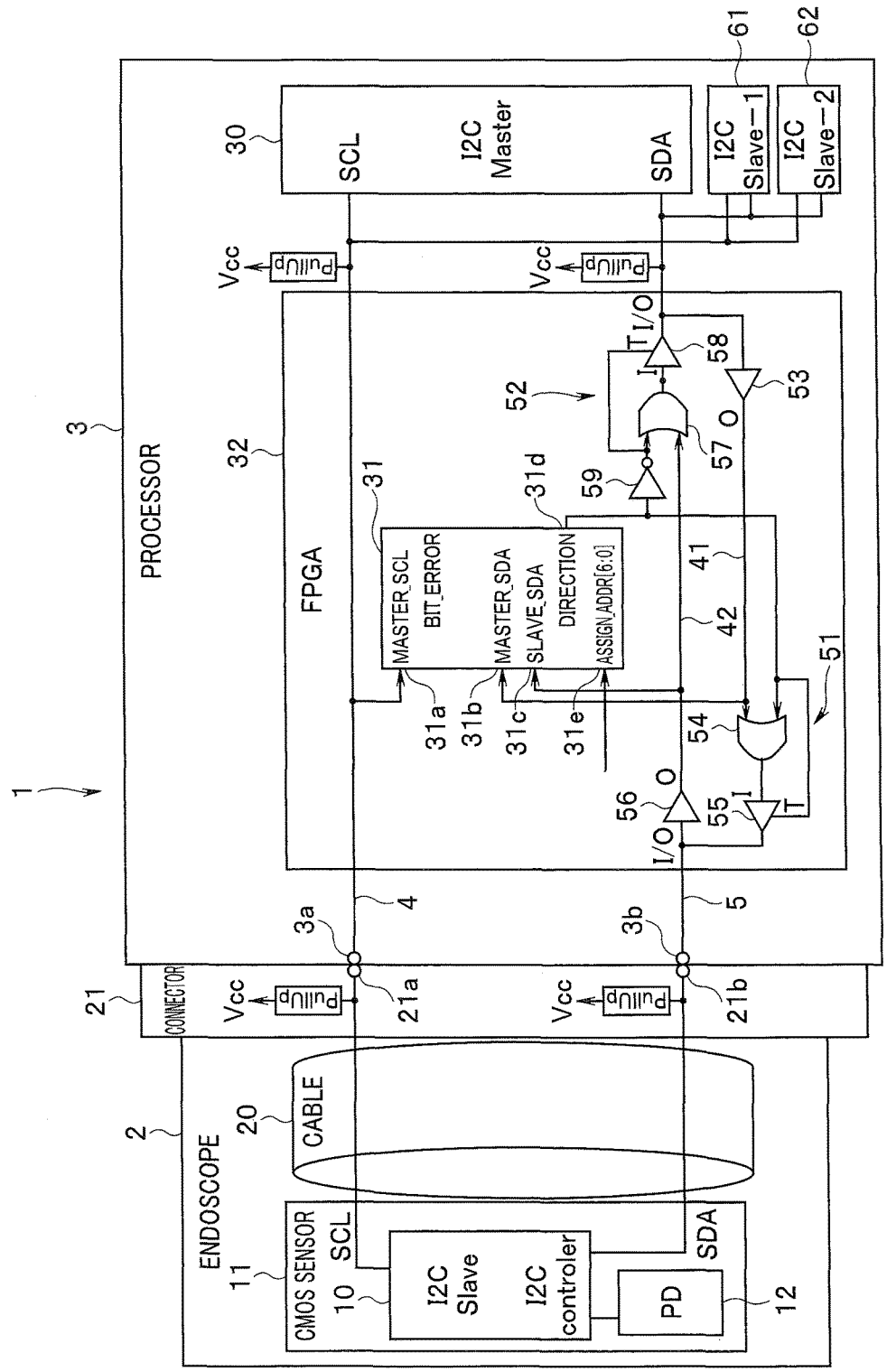
FIG. 1 is a diagram illustrating a configuration of an I2C system in an endoscope system of a first embodiment of the present invention.

FIG. 1 is a diagram illustrating a configuration of an I2C system in an endoscope system of a first embodiment of the present invention.

As illustrated in FIG. 1, in an endoscope system 1 which is the first embodiment of the present invention, a main part is configured by an endoscope 2 adopting a CMOS sensor as an image pickup device, and a processor 3 freely attachably and detachably connected to the endoscope 2 and configured to perform various kinds of signal processing relating to the endoscope 2.

The endoscope 2 includes a CMOS sensor 11 provided on a distal end of an insertion portion to be inserted to a subject and configured to pick up an optical image of the subject and output a predetermined digital image pickup signal, a cable 20 connected to the CMOS sensor 11 and configured to transmit a control signal to the CMOS sensor 11 or the like other than the digital image pickup signal, and a connector portion 21 disposed on the other end of the cable 20 to be connected to the processor 3.

The CMOS sensor 11 is configured including an image pickup portion 12 (PD 12) configured to pick up the optical image of the subject and generate a predetermined analog image pickup signal by a predetermined clock and a vertical synchronizing signal VD/a horizontal synchronizing signal HD generated in the processor 3, an AFE circuit provided with an A/D conversion portion configured to execute predetermined signal processing to the image pickup portion 12, perform conversion to a digital image pickup signal and output the signal, and not shown in the figure, and a P/S circuit configured to perform parallel/serial conversion of the digital image pickup signal from the AFE circuit and output the signal to a subsequent stage, and not shown in the figure.

As described above, while the endoscope in the present embodiment adopts the CMOS sensor 11 as the image pickup device, in the endoscope system of the present embodiment, the above-described I2C is applied to communication control between the CMOS sensor 11 disposed at an endoscope distal end and the processor 3 which is a signal processing portion.

In addition, in the present embodiment, the CMOS sensor 11 is one of slaves in I2C control, a master is mounted on the processor 3 on the other hand, and the master and the slave are connected by two serial bus signal lines (serial data SDA and serial clock SCL).

Then, in the case of the endoscope system like the present embodiment, the CMOS sensor which is one of the slaves disposed at an endoscope distal end portion and the processor 3 which is the master are connected by the cable 20 having a length of several meters and including a portion of the serial data SDA and the serial clock SCL inside.

On the other hand, as described above, the endoscope system of the present embodiment is often used near a strong noise source such as an electrocautery so that the cable connecting the master and the slave is exposed to strong noise.

That is, as described above, in the case that the strong noise of the electrocautery or the like is applied to the cable 20 connecting the master (processor) and the slave (CMOS sensor), even when the cable 20 has sufficient noise resistance, the serial clock SCL is in danger of being disturbed by the external noise, on a side of the slave (CMOS sensor) connected to an I2C bus in particular.

The present application is implemented in consideration of relating circumstances, and even when the serial clock SCL is disturbed by the external noise, a system freeze can be avoided.

Returning to FIG. 1, in the processor 3, an I2C master 30 as the master, to which the two serial bus signal lines (serial data SDA and serial clock SCL) are connected, is disposed.

On the other hand, in the CMOS sensor 11 disposed at the distal end of the endoscope 2, an I2C slave 10 as the slave, to which the two serial bus signal lines (serial data SDA and serial clock SCL) are connected similarly, is disposed. Note that the I2C slave 10 functions as an I2C controller configured to control the image pickup portion 12 (PD 12).

The two serial bus signal lines (serial data SDA and serial clock SCL) extended from the I2C slave 10 are inserted into the cable 20 inside the endoscope 2, and extended through the connector portion 21 into the processor 3.

The connector portion 21 includes a terminal 21a for the serial clock SCL and a terminal 21b for the serial data SDA, to be connected to a terminal 3a for the serial clock SCL or a terminal 3b for the serial data SDA provided in the opposite processor 3 respectively.

<Bus Signal Direction Switching Mechanism of Serial Data SDA>

Hereinafter, a direction switching mechanism of the bus signal of the serial data SDA in the present first embodiment will be described.

In the present first embodiment, between post stage of the terminal 3a for the serial clock SCL and the terminal 3b for the serial data SDA, and the I2C master 30 in the processor 3, a mechanism configured to switch a bus signal direction of the serial data SDA, that is, a direction of the bus signal between a first direction "master side→slave side" and a second direction "slave side→master side", is disposed.

The bus signal direction switching mechanism of the serial data SDA is configured by a so-called FPGA (field-programmable gate array) 32, and includes a first signal line 41 configured to transmit predetermined data from the I2C master 30 to the I2C slave 10, a second signal line 42 configured to transmit the predetermined data from the I2C slave 10 to the I2C master 30, a first signal line selection portion 51 and a second signal line selection portion 52 configured to select either one of the first signal line 41 and the second signal line 42 so as to be effective as a bus signal line of the serial data SDA, and a signal control portion 31 configured to control the selecting operation in the first signal line selection portion 51 and the second signal line selection portion 52.

Here, the first signal line 41 is a signal line used when the first direction "master side→slave side" is selected in the bus signal direction switching mechanism, the second signal line 42 is a signal line used when the second direction "slave side→master side" is selected, and specific routes of the first signal line 41 and the second signal line 42 will be described in detail later.

Note that, inside the processor 3, an I2C slave 61 and an I2C slave 62 functioning as the other slaves in the I2C system are provided.

The signal control portion 31 includes a terminal 31a configured to recive a master side serial clock SCL (MASTER_SCL) from a bus of the serial clock SCL, a terminal 31b configured to receive a master side serial data SDA (MASTER_SDA) from a bus (the first signal line 41 to be described later) of the serial data SDA, a terminal 31c configured to receive slave side serial data SDA (SLAVE_SDA) from a bus (the second signal line 42 to be described later) of the serial data SDA, a terminal 31d configured to output a bus signal direction switching signal (DIRECTION) of the serial data SDA, and a terminal 31e configured to receive a slave address (ASSIGN_ADDR) of the I2C slave 10 in the CMOS sensor 11, respectively.

The first signal line selection portion 51 includes a first OR circuit 54 and a first three-state buffer circuit 55 provided on the first signal line 41 in the serial data SDA, and a first buffer 56 provided on the second signal line 42 in the serial data SDA.

More specifically, to an input terminal of the first OR circuit 54 in the first signal line selection portion 51, an output terminal "O" of a second buffer 53 (to be described later) is connected and also the terminal 31*d* in the signal control portion 31 is connected, and a master side serial data SDA signal in the first signal line 41 and the bus signal direction switching signal DIRECTION outputted from the terminal 31*d* in the signal control portion 31 are inputted.

For the first three-state buffer circuit 55 in the first signal line selection portion 51, an output signal of the first OR circuit 54 is inputted to the input terminal "I", the bus signal direction switching signal DIRECTION outputted from the terminal 31*d* in the signal control portion 31 is inputted to a control input terminal "T", and an output signal from an output terminal "I/O" is controlled according to the bus signal direction switching signal DIRECTION.

To an input end of the first buffer 56 in the first signal line selection portion 51, the slave side serial data SDA inputted from the terminal 3*a* for the serial clock SCL on the second signal line 42 is inputted, and the output terminal "I/O" of the first three-state buffer circuit 55 is connected. Note that the output terminal "0" of the first buffer 56 is connected to an input terminal of a second OR circuit 57 (to be described later).

On the other hand, the second signal line selection portion 52 includes the second OR circuit 57 and a second three-state buffer circuit 58 provided on the second signal line 42 in the serial data SDA, the second buffer 53 provided on the first signal line 41 in the serial data SDA, and an inverter circuit 59 provided between the terminal 31*d* in the signal control portion 31 and the second OR circuit 57.

More specifically, to the input terminal of the second OR circuit 57 in the second signal line selection portion 52, the output terminal "0" of the first buffer 56 is connected and also the terminal 31*d* in the signal control portion 31 is connected, and the output signal of the first buffer 56 which is the slave side serial data SDA signal in the second signal line 42 and the bus signal direction switching signal DIRECTION outputted from the terminal 31*d* in the signal control portion 31 and inverted by the inverter circuit 59 are inputted.

For the second three-state buffer circuit 58 in the second signal line selection portion 52, an output signal of the second OR circuit 57 is inputted to the input terminal "I", the bus signal direction switching signal DIRECTION outputted from the terminal 31*d* in the signal control portion 31 and inverted by the inverter circuit 59 is inputted to the control input terminal "T", and the output signal from the output terminal "I/0" is controlled according to the inverted bus signal direction switching signal DIRECTION.

To an input end of the second buffer 53 in the second signal line selection portion 52, the master side serial data SDA inputted from a side of the I2C master 30 on the first signal line 41 is inputted, and the output terminal "I/O" of the second three-state buffer circuit 58 is connected. Note that the output terminal "O" of the second buffer 53 is connected to the input terminal of the first OR circuit 54, and input is performed as the master side serial data SDA.

The inverter circuit 59 in the second signal line selection portion 52 receives input of the bus signal direction switching signal DIRECTION outputted from the terminal 31*d* in the signal control portion 31, and inputs inverted output to the second OR circuit 57.

<Structure of Bus Signal Direction Switching Mechanism of Serial Data SDA>

A structure of the direction switching mechanism of the bus signal of the serial data SDA described above will be described.

Figure 2:
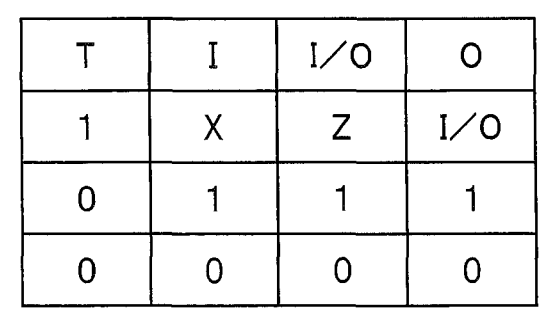

FIG. 2 is a truth table of a logic circuit in the first three-state buffer circuit 55 and the second three-state buffer circuit 58 in the first signal line selection portion 51 and the second signal line selection portion 52.

As described above, the bus signal direction switching signal DIRECTION is inputted to the control input terminal "T" in the first three-state buffer circuit 55 in the first signal line selection portion 51, and on the other hand, the bus signal direction switching signal DIRECTION inverted by the inverter circuit 59 is inputted to the control input terminal "T" in the second three-state buffer circuit 58 in the second signal line selection portion 52.

In addition, in the present first embodiment, from the terminal 31*d* of the signal control portion 31, an "L" signal is outputted when the first direction is selected (master-→slave) and an "H" signal is outputted when the second direction is selected (slave→master) on the other hand.

Here, as illustrated in the truth table in FIG. 2, when the "H" signal is inputted to the control input terminal "T" of the first three-state buffer circuit 55 or the second three-state buffer circuit 58, the output terminal "I/O" becomes high impedance "Z" regardless of a state of the input signal. At the time, the output terminal "O" of the second buffer 53 or the first buffer 56 outputs the inputted signal as it is.

Specifically, for example, it is assumed now that the signal control portion 31 selects the first direction "master side-→slave side" using the first signal line 41 as the bus signal direction switching mechanism.

At the time, the signal control portion 31 outputs the "L" signal for selecting the first direction as the bus signal direction switching signal DIRECTION from the DIRECTION terminal 31*d*.

Then, the bus signal direction switching signal DIRECTION is inputted as the "L" signal to the control input terminal "T" of the first three-state buffer circuit 55 on one hand, and inputted to the inverter circuit 59 and inverted by the inverter circuit 59 on the other hand, and thus the "H" signal is inputted to the control input terminal "T" of the second three-state buffer circuit 58.

Then, as described above, the output terminal "I/O" in the second three-state buffer circuit 58 becomes the high impedance "Z", and the signal from the I2C master 30 in the master side serial data SDA flows to the side of the second buffer 53. Then, at the output terminal "O" in the second buffer 53, the master side serial data SDA inputted from the side of the I2C master 30 appears as it is.

On the other hand, to the control input terminal "T" of the first three-state buffer circuit 55, as described above, the bus signal direction switching signal DIRECTION in an "L" state outputted from the terminal 31*d* of the signal control portion 31 is inputted.

At the time, to the output terminal "I/O" in the first three-state buffer circuit 55, the signal inputted to the input terminal "I", the master side serial data SDA inputted from the side of the I2C master 30 through the second buffer 53 in this case, is outputted as it is.

Here, in the present embodiment, the route of the I2C master 30→the second buffer 53→the first OR circuit 54→the first three-state buffer circuit 55→the terminal 3*b* for the serial data SDA is defined as the first signal line 41.

That is, as the bus signal direction switching mechanism, when switching to the first direction "master side→slave side" is desired, the first signal line 41 can be selected by the above-described structure.

On the other hand, for example, it is assumed now that the signal control portion 31 selects the second direction "slave side→master side" using the second signal line 42 as the bus signal direction switching mechanism.

At the time, the signal control portion 31 outputs the "H" signal for selecting the first direction as the bus signal direction switching signal DIRECTION from the DIRECTION terminal 31d.

Then, the bus signal direction switching signal DIRECTION is inputted as the "H" signal to the control input terminal "T" of the first three-state buffer circuit 55 on one hand, and inputted to the inverter circuit 59 and inverted by the inverter circuit 59 on the other hand, and thus the "L" signal is inputted to the control input terminal "T" of the second three-state buffer circuit 58.

Then, contrary to the above description, the output terminal "I/O" in the first three-state buffer circuit 55 becomes the high impedance "Z", and the signal from the I2C slave 10 in the slave side serial data SDA flows to the side of the first buffer 56. Then, at the output terminal "O" in the first buffer 56, the slave side serial data SDA inputted from the side of the I2C slave 10 appears as it is.

On the other hand, to the control input terminal "T" of the second three-state buffer circuit 58, as described above, the bus signal direction switching signal DIRECTION in the "L" state through the inverter circuit 59 is inputted.

At the time, to the output terminal "I/O" in the second three-state buffer circuit 58, the signal inputted to the input terminal "I", the slave side serial data SDA inputted from the side of the I2C slave 10 through the first buffer 56 in this case, is outputted as it is.

Here, in the present embodiment, the route of the I2C slave 10→the terminal 3b for the serial data SDA→the first buffer 56→the second OR circuit 57→the second three-state buffer circuit 58→the I2C master 30 is defined as the second signal line 42.

That is, as the bus signal direction switching mechanism, when switching to the second direction "slave side→master side" is desired, the second signal line 42 can be selected by the above-described structure.

<Actions of First Embodiment>

Next, actions of the present first embodiment will be described.

<Fixation of Bus Signal Direction of Serial Clock SCL>

While the present first embodiment adopts the I2C system to the communication control of the master side (the I2C master 30) disposed in the processor 3 and the slave side (the I2C slave 10 in the CMOS sensor 11) disposed in the endoscope 2, in the present first embodiment, the serial clock SCL is fixed to "master side→slave side" at all times first.

<Switching Action of Bus Signal Direction of Serial Data SDA>

In the present first embodiment, by the above-described bus signal direction switching mechanism, the direction of the bus signal in the serial data SDA is set to the first direction "master side→slave side" as a general rule, and the direction of the bus signal in the serial data SDA is set to the second direction "slave side→master side" only at the time of a reception bit at which the side of the I2C master 30 receives the data from the I2C slave 10 in the CMOS sensor 11 (for example, Ack or ReadData).

Figure 3:
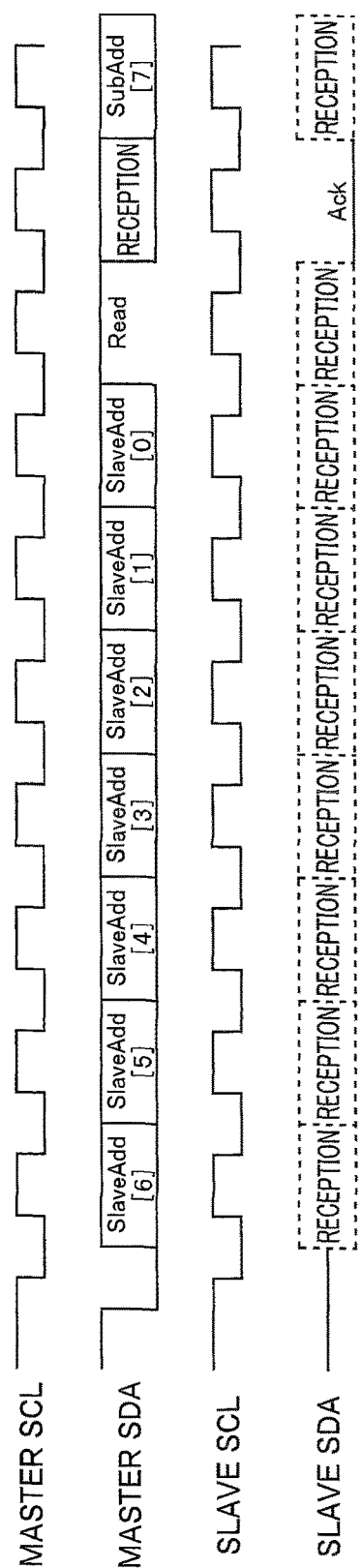
FIG. 3 is a timing chart illustrating a state of each serial bus signal at normal time, in the endoscope system of the first embodiment.

FIG. 3 is a timing chart illustrating a state of each serial bus signal at normal time, in the endoscope system of the first embodiment.

FIG. 3 illustrates a situation where the predetermined data is transmitted from the I2C master 30 to the I2C slave 10 in the CMOS sensor 11 by the master serial data SDA (MASTER_SDA) according to the master serial clock (MASTER_SCL) from the I2C master 30.

As described above, since the direction of the bus signal in the serial data SDA is set to the first direction "master side→slave side" in the present embodiment, the signal control portion 31 selects the first direction "master side→slave side" using the first signal line 41 as the bus signal direction switching mechanism.

That is, the signal control portion 31 outputs the "L" signal for selecting the first direction as the bus signal direction switching signal DIRECTION from the DIRECTION terminal 31d.

Thus, the "H" signal inverted by the inverter circuit 59 is inputted to the control input terminal "T" of the second three-state buffer circuit 58, and the "L" signal is inputted to the control input terminal "T" of the first three-state buffer circuit 55 on the other hand.

At the time, as described above, the output terminal "I/O" in the second three-state buffer circuit 58 becomes the high impedance "Z", the signal from the I2C master 30 in the master side serial data SDA flows to the side of the second buffer 53, and the master side serial data SDA inputted from the side of the I2C master 30 is outputted as it is to the terminal 3b for the serial data SDA through the second buffer 53 and the first three-state buffer circuit 55.

In FIG. 3, when the data for eight bits is transmitted from the I2C master 30 in the MASTER_SDA, the first direction "master side→slave side" using the first signal line 41 is selected as described above.

On the other hand, at the time of the reception bit at which the I2C master 30 receives the data from the side of the I2C slave 10 of the CMOS sensor 11, which is the next bit after transmission of the data for eight bits is ended, at the time of Ack in this case, the signal control portion 31 selects the second direction "slave side→master side" using the second signal line 42 as the bus signal direction switching mechanism.

That is, the signal control portion 31 outputs the "H" signal for selecting the second direction as the bus signal direction switching signal DIRECTION from the DIRECTION terminal 31d.

Thus, the "L" signal inverted by the inverter circuit 59 is inputted to the control input terminal "T" of the second three-state buffer circuit 58, and the "H" signal is inputted to the control input terminal "T" of the first three-state buffer circuit 55 on the other hand.

At the time, as described above, the output terminal "I/O" in the first three-state buffer circuit 55 becomes the high impedance "Z", the signal from the I2C slave 10 in the slave side serial data SDA flows to the side of the first buffer 56, and the slave side serial data SDA inputted from the side of the I2C slave 10 is outputted as it is to the I2C master 30 through the first buffer 56 and the second three-state buffer circuit 58.

In FIG. 3, when the I2C master 30 receives the Ack signal from the SLAVE_SDA in the MASTER_SDA, the second direction "slave side→master side" using the second signal line 42 is selected as described above.

Next, in what state each serial bus signal is when an abnormal signal is applied onto the serial clock SCL bus when it is assumed that the bus signal direction switching mechanism in the present embodiment described above is not provided will be described.

Figure 4:
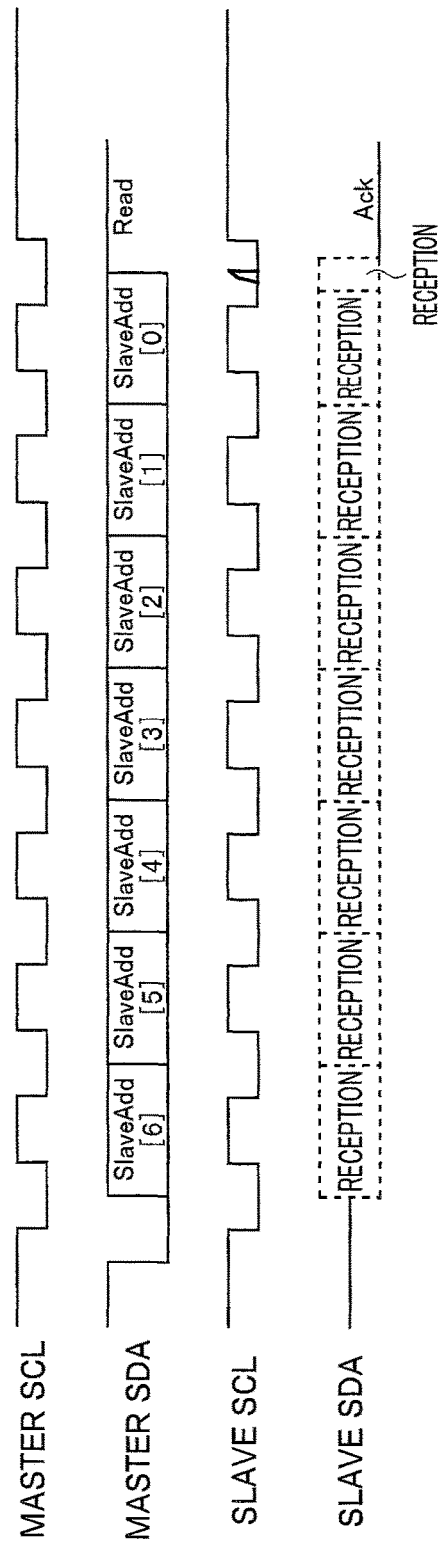
FIG. 4 is a timing chart illustrating a state of each serial bus signal when an abnormal signal is applied onto a serial clock SCL bus when it is assumed that the bus signal direction switching mechanism of the serial data SDA is not provided, in the endoscope system of the first embodiment.

FIG. 4 is a timing chart illustrating the state of each serial bus signal when the abnormal signal is applied onto the serial clock SCL bus in the case of assuming that the bus signal direction switching mechanism of the serial data SDA is not provided in the endoscope system of the first embodiment.

The endoscope system like the present embodiment is often used near the noise source such as the so-called electrocautery, and the cable 20 connecting the I2C slave 10 in the CMOS sensor 11 and the I2C master 30 in the processor 3 and including a portion of the serial data SDA and the serial clock SCL inside is exposed to the noise of the kind.

Then, as described above, since a peripheral device such as the electrocautery can be a relatively strong noise source, even when the cable 20 has the sufficient noise resistance, a risk of erroneously recognizing the external noise as a rising edge of the serial clock SCL on the side of the I2C slave 10 (CMOS sensor) in particular in the serial clock SCL.

FIG. 4 illustrates the situation in the case that the I2C system erroneously recognizes the external noise as the rising edge of the serial clock SCL, in the slave side serial clock SCL (SLAVE_SCL).

As illustrated in FIG. 4, due to the external noise, on the side of the I2C slave 10, it seems that one more serial clock SCL is present, causing a bit shift. On the other hand, on the side of the I2C master 30, it seems that 1 b (Read) and 0 b (Ack) are colliding.

Incidentally, in the I2C, since it is assumed that collision detection is performed in a multi-master bus and bus mediation (mediation of ownership of the bus) is performed by bus arbitration, in the case that a collision occurs on the I2C bus, it is interpreted that the plurality of masters are simultaneously accessing, and the collision of the other masters with each other is guaranteed so that no problem arises.

However, in the I2C system, as illustrated in FIG. 4, the collision due to the bit shift between the master and the slave is an unexpected behavior.

Therefore, when it is assumed that the bus signal direction switching mechanism of the serial data SDA like the present embodiment is not provided, in the case of erroneously recognizing the external noise as the rising edge of the serial clock SCL, the processor which is the master misunderstands as simultaneous access with the other master, and stops the serial clock SCL and the serial data SDA, that is, turns the bus to a free state.

Then, in the case that stop timing of the serial clock SCL and the serial data SDA by the I2C master 30 overlaps with L drive (by the above-described Ack, for example) on a slave side, the serial data SDA is stopped while being kept pulled to "L" so that the bus becomes a busy state and cannot return.

That is, since the bus continuously looks as if in the busy state from the I2C master 30, the I2C master 30 keeps standing by and does not return, falling into a so-called system freeze state. As a result, inconvenience arises in which the I2C master 30 cannot access the slave other than the I2C slave 10 (CMOS sensor 11).

Figure 5:
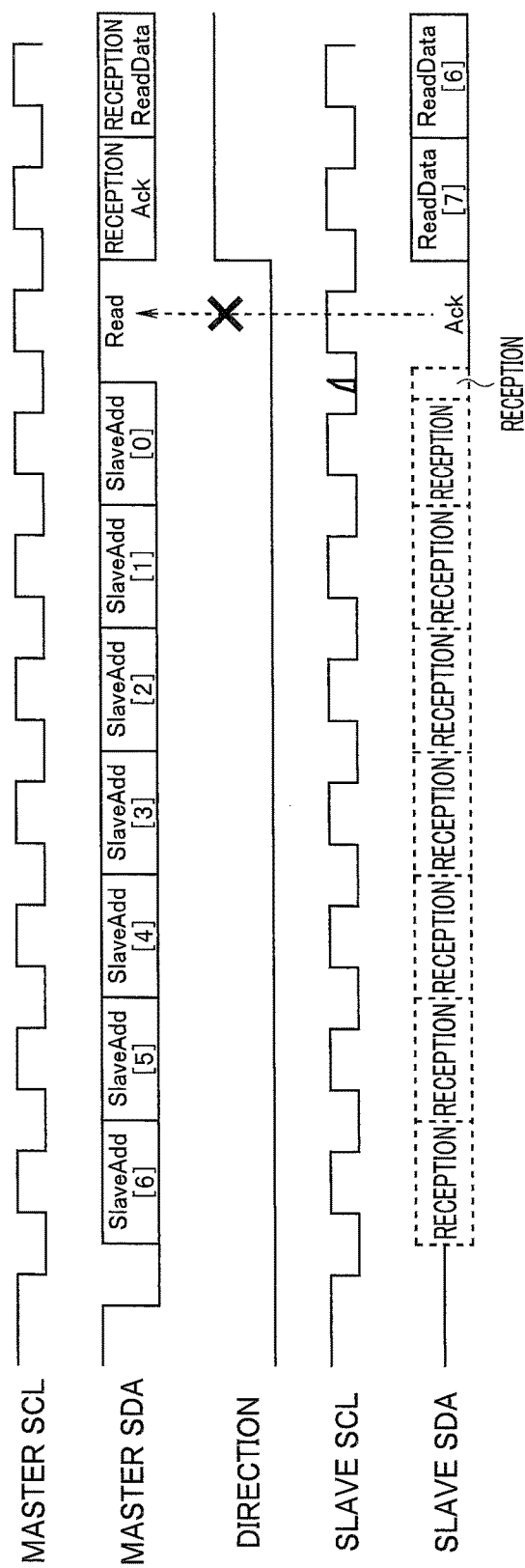
FIG. 5 is a timing chart illustrating a state of each serial bus signal when the abnormal signal is applied onto the serial clock SCL bus, in the endoscope system of the first embodiment.

FIG. 5 describes the state of each serial bus signal when the abnormal signal is applied onto the serial clock SCL bus in the present first embodiment including the bus signal direction switching mechanism configured as described above.

As described above, in the present first embodiment, the direction of the bus signal in the serial data SDA is set to the first direction "master side→slave side" as the general rule by the bus signal direction switching mechanism. That is, the bus signal direction switching signal DIRECTION from the signal control portion 31 is set to the "L" state.

Then, the direction of the bus signal in the serial data SDA is set to the second direction "slave side→master side" only at the time of the reception bit at which the side of the I2C master 30 receives the data from the I2C slave 10 in the CMOS sensor 11 (for example, Ack or ReadData).

Thus, even when the external noise is mixed in the SLAVE_SCL at the timing illustrated in FIG. 4, it seems one more serial clock SCL is present and a pseudo clock is generated, since the bus signal direction switching signal DIRECTION is still in the "L" state at the timing at which the pseudo clock is generated, even when an Ack signal is transmitted from the I2C slave 10 to the I2C master 30 immediately after the timing, the I2C master 30 does not receive the Ack signal as long as the bus signal direction switching signal DIRECTION is in the "L" state.

Thereafter, even when ReadData is transmitted from the I2C slave 10 to the I2C master 30 in the serial data SDA (at the time, the signal control portion 31 turns the bus signal direction switching signal DIRECTION to the "H" state, selecting the second direction "slave side→master side"), the I2C master 30 receives ReadData in the state of not receiving the Ack signal and thus performs processing as NoAck.

That is, the I2C master 30 defines that ReadData is received at NoAck and issues a Stop bit, both bit sequences are reset, and Read processing is performed again.

Then, as illustrated in FIG. 5, when the received ReadData is 0 b, the I2C master 30 interprets it as Ack and reads Data shifted by one bit, however, by contriving a soft sequence of the I2C master 30 for Read of the erroneous Data, such as confirmation by reading two or three times, the above-described inconvenience as illustrated in FIG. 4 can be avoided.

As described above, according to the present embodiment, in the communication system in the endoscope system including the endoscope loaded with the CMOS sensor as the image pickup device, occurrence of the system freeze due to the external noise can be avoided.

Note that, in the above-described embodiment, the bus signal direction switching mechanism of the serial data SDA configured by the FPGA 32 is provided inside the processor 3, however, a disposing position of the bus signal direction switching mechanism is not limited to the processor 3. That is, even when the bus signal direction switching mechanism is disposed between the I2C master 30 and the I2C slave 10, in the connector portion 21 or an operation portion or the like on the side of the endoscope 2 for example, same effects can be demonstrated.

Furthermore, the present invention is not limited to the above-described embodiment, various changes and modifications or the like are possible without changing the gist of the present invention, and the embodiment configured by partially combining the above-described embodiment or the like also belongs to the present invention.

What is claimed is:

1. A communication system wherein a slave device and a master device configured to transmit and receive data to/from the slave device by specifying an address are connected by a clock signal line configured to convey a clock transmitted from the master device and a serial data signal line configured to bidirectionally transmit data, the communication system comprising:

a first signal line configuring a portion of the serial data signal line and configured to transmit predetermined data from the master device to the slave device;
a second signal line configuring a portion of the serial data signal line and configured to transmit predetermined data from the slave device to the master device;
a signal line selection portion configured to select either one of the first signal line and the second signal line so as to be effective as the serial data signal line; and
a signal control portion including a terminal configured to output a signal direction switching signal for controlling the selecting operation in the signal line selection portion,
wherein the signal line selection portion is configured by a first signal line selection portion and a second signal line selection portion,
the first signal line selection portion includes a first OR circuit and a first three-state buffer circuit provided on the first signal line, and a first buffer provided on the second signal line, and
the second signal line selection portion includes a second OR circuit and a second three-state buffer circuit provided on the second signal line, a second buffer provided on the first signal line, and an inverter circuit provided between the terminal of the signal control portion and the second OR circuit.

2. The communication system according to claim 1,
wherein the signal control portion controls the selecting operation in the signal line selection portion to select either one of the first signal line and the second signal line so as to be effective as the serial data signal line, according to a kind of the data transmitted and received between the master device and the slave device in the serial data signal line.

3. The communication system according to claim 1, wherein the signal control portion controls the selecting operation in the signal line selection portion to select the first signal line so as to be effective as the serial data signal line when the predetermined data is transmitted from the master device to the slave device, and to select the second signal line so as to be effective as the serial data signal line only at a time of a reception bit at which the master device receives the predetermined data from the slave device.

4. The communication system according to claim 1, wherein the signal control portion outputs the signal direction switching signal at a predetermined signal level to the signal line selection portion in a case that the first signal line is effective as the serial data signal line, and outputs the signal direction switching signal for which the predetermined signal level is inverted to the signal line selection portion in a case that the second signal line is effective as the serial data signal line.

5. The communication system according to claim 1,
wherein an output terminal of the second buffer is connected to one of two input terminals of the first OR circuit, and
the terminal of the signal control portion is connected to another of the two input terminals of the first OR circuit.

6. The communication system according to claim 1,
wherein an output terminal of the first OR circuit is connected to an input terminal of the first three-state buffer circuit, and
the terminal of the signal control portion is connected to a control input terminal of the first three-state buffer circuit.

7. The communication system according to claim 6, wherein the first three-state buffer circuit controls an output signal from the output terminal, according to the signal direction switching signal outputted from the terminal of the signal control portion.

8. The communication system according to claim 1,
wherein the terminal of the signal control portion is connected to an input terminal of the inverter circuit,
an output terminal of the first buffer is connected to one of two input terminals of the second OR circuit, and
an output terminal of the inverter circuit is connected to another of the two input terminals of the second OR circuit.

9. The communication system according to claim 1,
wherein an output terminal of the second OR circuit is connected to an input terminal of the second three-state buffer circuit, and
the output terminal of the inverter circuit is connected to a control input terminal of the second three-state buffer circuit.

10. The communication system according to claim 9, wherein the second three-state buffer circuit controls an output signal from the output terminal, according to the signal direction switching signal outputted from the terminal of the signal control portion and inverted by the inverter circuit.

* * * * *